(12) United States Patent
Dickie

(10) Patent No.: US 8,590,091 B2
(45) Date of Patent: Nov. 26, 2013

(54) DUAL MOTION POWERED TOOTHBRUSH

(75) Inventor: Robert G. Dickie, King City (CA)

(73) Assignee: Brushpoint Innovations Inc, King, Ontario (CA)

( * ) Notice: Subject to any disclaimer, the term of this patent is extended or adjusted under 35 U.S.C. 154(b) by 371 days.

(21) Appl. No.: 12/962,100

(22) Filed: Dec. 7, 2010

(65) Prior Publication Data

US 2012/0137452 A1   Jun. 7, 2012

(51) Int. Cl.
*A46B 13/02* (2006.01)
*A61C 17/34* (2006.01)

(52) U.S. Cl.
USPC ................................. 15/22.1; 15/22.4; 15/28

(58) Field of Classification Search
USPC .................. 15/22.1, 22.2, 22.4, 28
See application file for complete search history.

(56) References Cited

U.S. PATENT DOCUMENTS

| 6,725,490 | B2 | 4/2004 | Blaustein et al. |
| 7,140,058 | B2 | 11/2006 | Gatzemeyer et al. |
| 7,698,771 | B2 * | 4/2010 | Gall ............................. 15/22.1 |
| 2003/0084525 | A1 | 5/2003 | Blaustein et al. |

* cited by examiner

*Primary Examiner* — Randall Chin
(74) *Attorney, Agent, or Firm* — Sand & Sebolt

(57) ABSTRACT

A replaceable brush head for a powered toothbrush and a toothbrush incorporating the same. The brush head includes a body having a bore extending therethrough and a driveshaft extending through the bore and rotatable about a longitudinal axis. A first bristle block is disposed in the body and is operatively engaged with the driveshaft. A second bristle block is disposed in the body and is operatively engaged with the first bristle block. Rotation of the driveshaft produces a first type of motion in the first bristle block and the motion of the first bristle block produces a second type of motion in the second bristle block.

17 Claims, 15 Drawing Sheets

DUAL MOTION POWERED TOOTHBRUSH

BACKGROUND OF THE INVENTION

1. Technical Field

The present application is directed generally to oral hygiene products. More particularly, this application is directed to a powered toothbrush. Specifically, this application is directed to a powered toothbrush having a replaceable brush head including a driveshaft with a cam, where the cam causes a first bristle block to move in a first manner, and the first bristle block in turn causes a second bristle block to move in a second manner.

2. Background Information

Dentists have advocated for some time that people should brush their teeth for at least two minutes using circular motions to remove plaque from their teeth. Making effective circular motions was fairly difficult for the average person when the toothbrush being used was a manual brush. This type of brushing motion became much easier with the advent of powered brushes that include rotatable bristle blocks. It has been recognized that simply rotating bristles on the teeth is insufficient to adequately clean the teeth. Consequently, powered toothbrushes have been developed where more complex bristle motions are undertaken. An example of one type of powered toothbrush that exhibits these complex motions is that shown in U.S. Pat. No. 6,725,490 issued to Blaustein et al. The '490 patent discloses a powered toothbrush which has a first bristle holder and a second bristle holder. A first cam and second cam are provided on a rotatable driveshaft. The first cam engages the first bristle holder and the second cam engages the second bristle holder. As the shaft rotates, the first cam and second cam cause the first and second bristle holders to move. In a preferred embodiment of the invention, the first bristle holder is caused by a first cam on the driveshaft to oscillate or vibrate about an axis that is generally perpendicular to the longitudinal axis of the driveshaft. The second bristle holder is moved by a second cam on the driveshaft in a direction that is generally parallel with the axis of rotation of the first bristle holder.

While the previously known devices provide a variety of complex bristle movements for cleaning teeth, there is room in the art for another powered toothbrush where the bristles are moved in a variety of ways so as to more effectively clean teeth.

SUMMARY OF THE INVENTION

The device of the present invention comprises a replaceable brush head for a powered toothbrush and a toothbrush incorporating the same. The brush head includes a body having a bore extending therethrough. A driveshaft extends through the bore and is rotatable about a longitudinal axis. A first bristle block is disposed in the body and is operatively engaged with the driveshaft. A second bristle block is disposed in the body and is operatively engaged with the first bristle block. Rotation of the driveshaft produces a first type of motion in the first bristle block and the moving first bristle block causes a second type of motion in the second bristle block.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

FIG. 5b is an end view of the first bristle block of FIG. 5a;

FIG. 6b is an end view of the second bristle block of FIG. 6a;

DETAILED DESCRIPTION OF THE INVENTION

Referring to FIGS. 1-13, there is shown a toothbrush in accordance with the present invention and generally indicated at 10. Toothbrush 10 is comprised of a powered handle 12 and a replaceable brush head generally indicated at 14.

Figure 7:
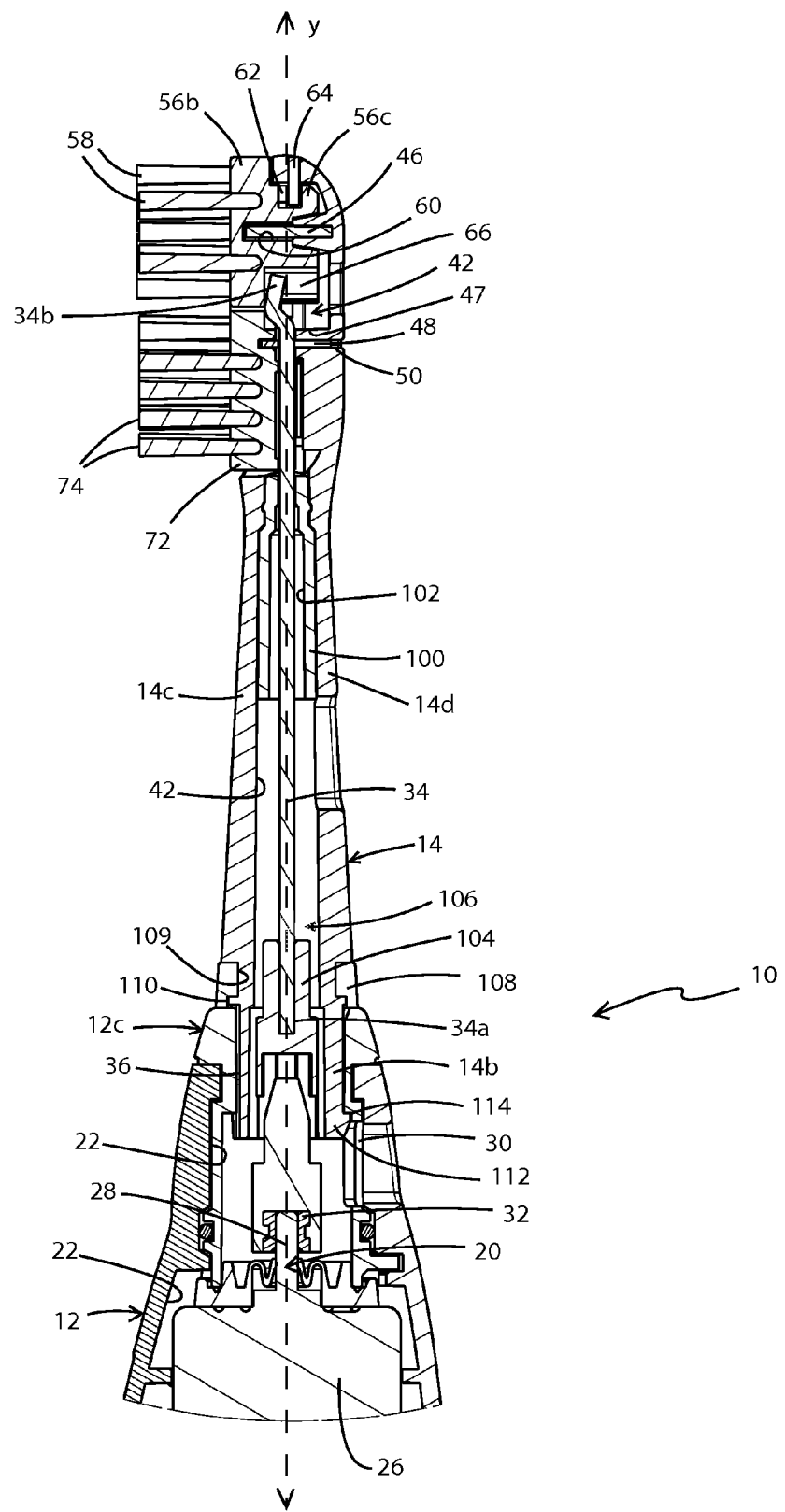
FIG. 7 is a cross-sectional side view of the brush head engaged with an upper portion of the powered handle.

Handle 12 may take any one of a number of configurations and includes a front region 12a, a back region 12b, a top end 12c and a bottom end 12d. Front and back regions 12a, 12b may be molded as individual pieces and then connected together along side seams 16 (FIG. 2) by an adhesive, hot welding or any other connection means. Alternatively, front and back regions 12a, 12b may be integrally molded as a single unit. An on/off switch 18 is provided on front region 12a and is operationally connected to a drive assembly 20 (FIG. 7) disposed within an interior cavity 22 of handle 14. Drive assembly 20 includes a motor 26 and a suitable power source (not shown). The power source may be a rechargeable power source or may be one or more batteries that are housed within cavity 22. A motor driveshaft 28 extends outwardly from motor 26 and terminates in a rotatable connector assembly 30. A bushing 32 is disposed between motor driveshaft 28 and connector assembly 30. Although not shown herein, connector assembly 30 defines a bore in at least a top region thereof. The bore is configured to receive a lower end 34a of a driveshaft 34 extending outwardly from head 14 therein as will be hereinafter described. The upper end 12c of handle 12 is configured to engage a bottom end 14b of brush head 14. FIG. 7 shows that upper end 12c defines an opening 36 to cavity 22. Bottom end 14b of brush head 14 has a diameter that is substantially identical to that of opening 36 so that bottom end 14b is tightly retained therein.

Figure 3:
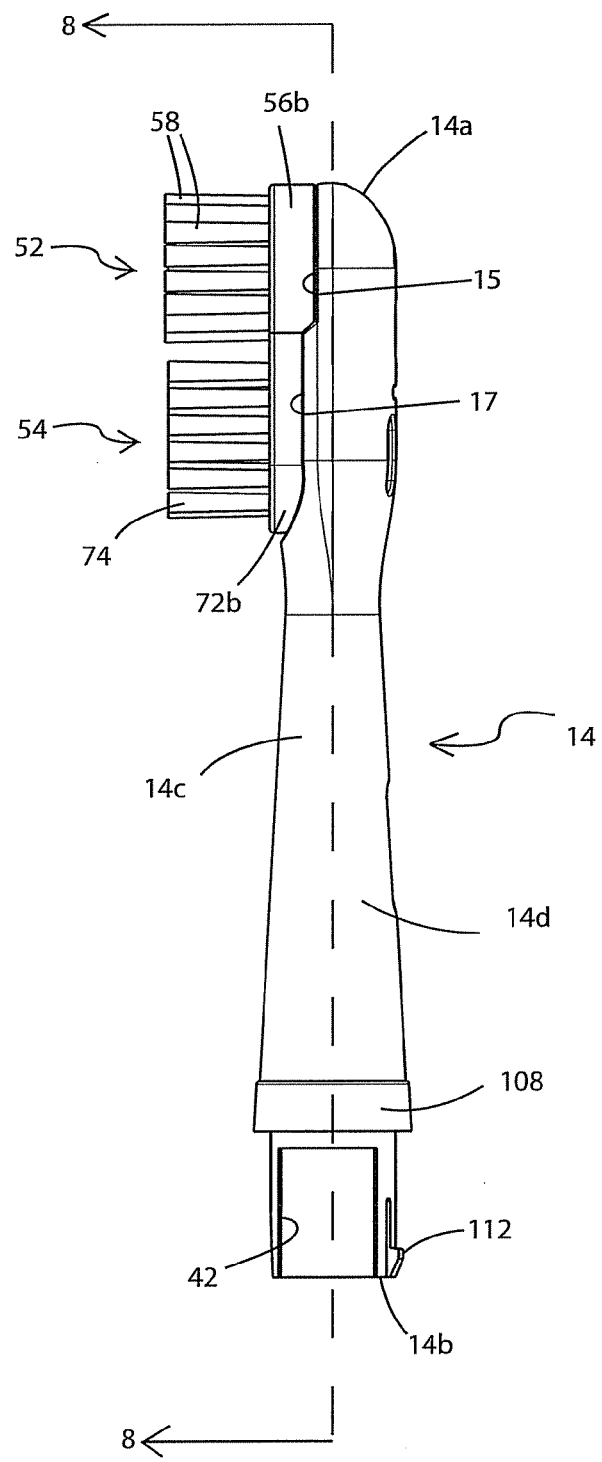
FIG. 3 is a side view of the brush head only.
Figure 4:
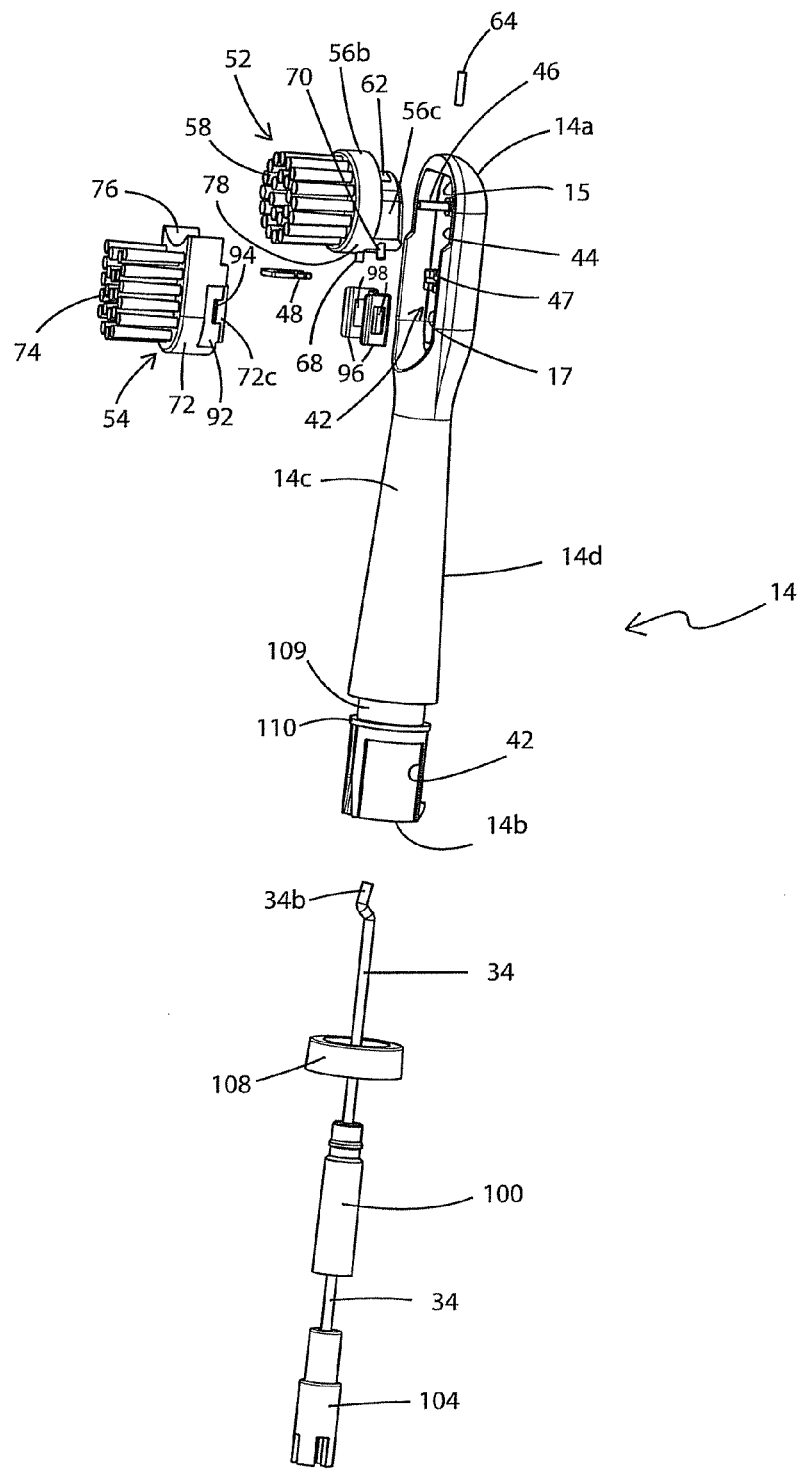
FIG. 4 is an exploded front perspective view of the brush head of FIG. 3.

Head 14 is shown in greater detail in FIGS. 3, 4 and 7. Head 14 has a top end 14a, bottom end 14b, a front region 14c and a back region 14d. Head 14 has a longitudinal axis "Y" (FIG. 7) that extends between top and bottom ends 14a, 14b. Preferably, head 14 is a unitary molded component such as is shown in FIG. 4 but it will be understood that front region 14c and back region 14d may be separately molded and then joined together to form head 14. Head 14 defines an interior cavity 42 (FIG. 8) that extends from proximate top end 14a to proximate bottom end 14b. A generally elliptical opening 44 to cavity 42 is defined in head 14 proximate top end 14a thereof. A pivot rod 46 extends outwardly and forwardly from an interior surface of back region 14d and into opening 44. A support 47 (FIGS. 4 and 8) extends outwardly and forwardly from the interior wall of back region 14d a spaced distance downwardly from pivot rod 46 and generally parallel thereto. Support 47 includes an aperture 50 therethrough. A connector member 48 is received through aperture 50 and extends forwardly and outwardly therefrom, projecting forwardly from the interior surface of back region 14d and into opening 44. Connector member 48 is spaced a distance vertically downwardly from pivot rod 46. Both of the pivot rod 46 and connector member 48 are disposed generally at right angles to the longitudinal axis "Y" of head 14.

Figure 1:
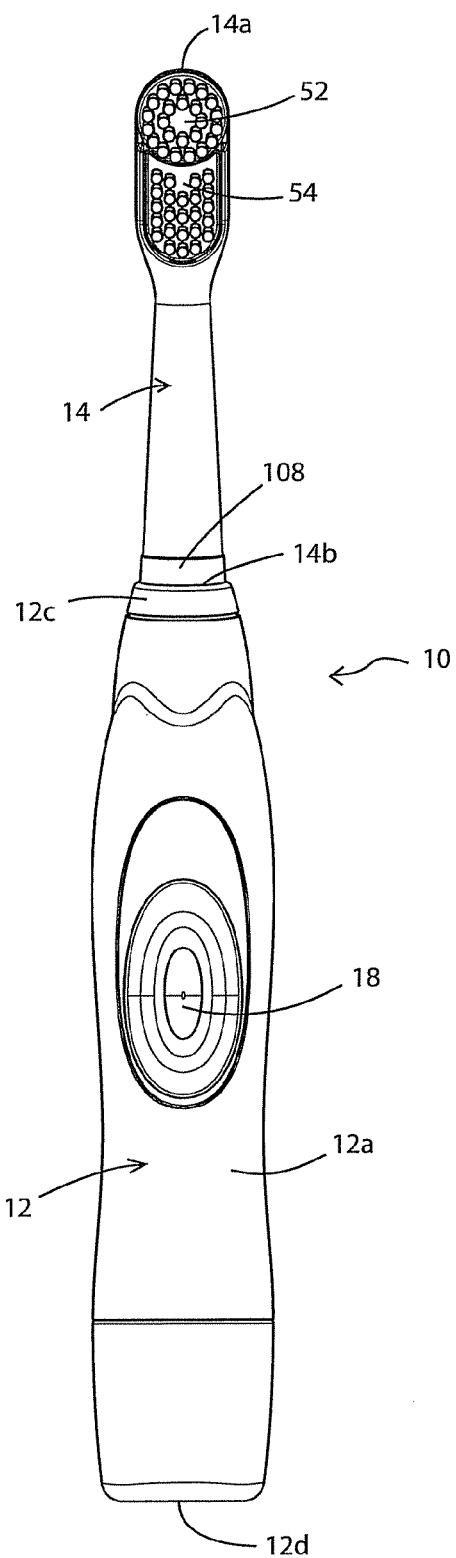
FIG. 1 is a front view of a powered toothbrush incorporating the brush head of the present invention.
Figure 2:
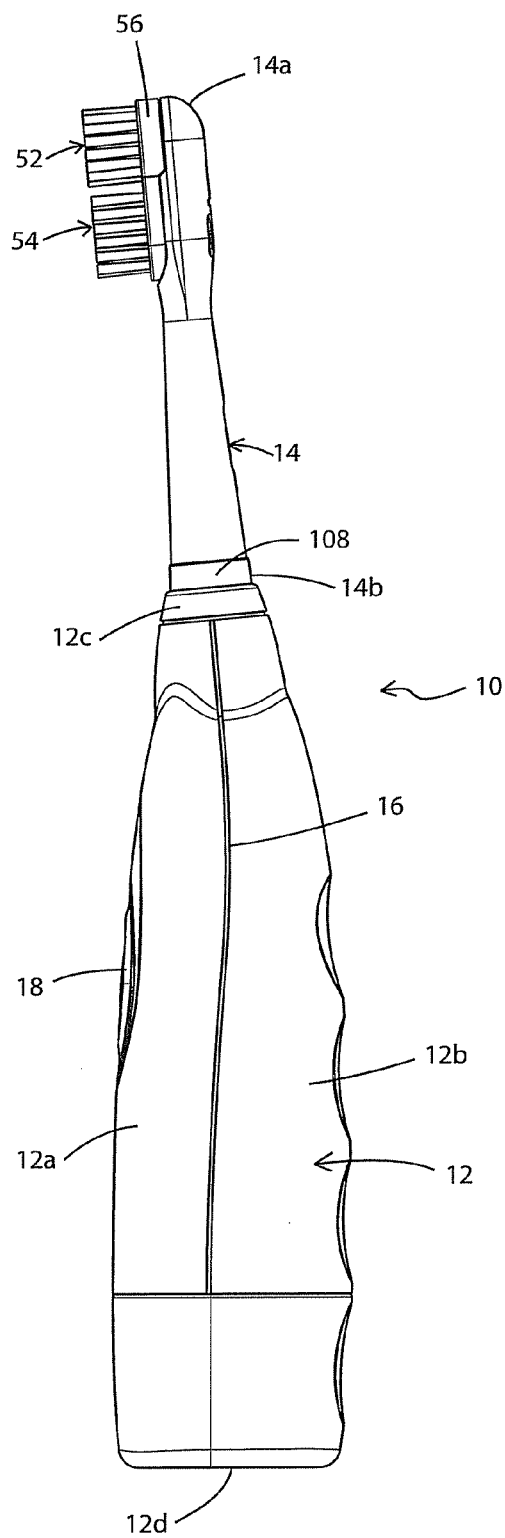
FIG. 2 is a side view of the toothbrush of FIG. 1.
Figure 5A:
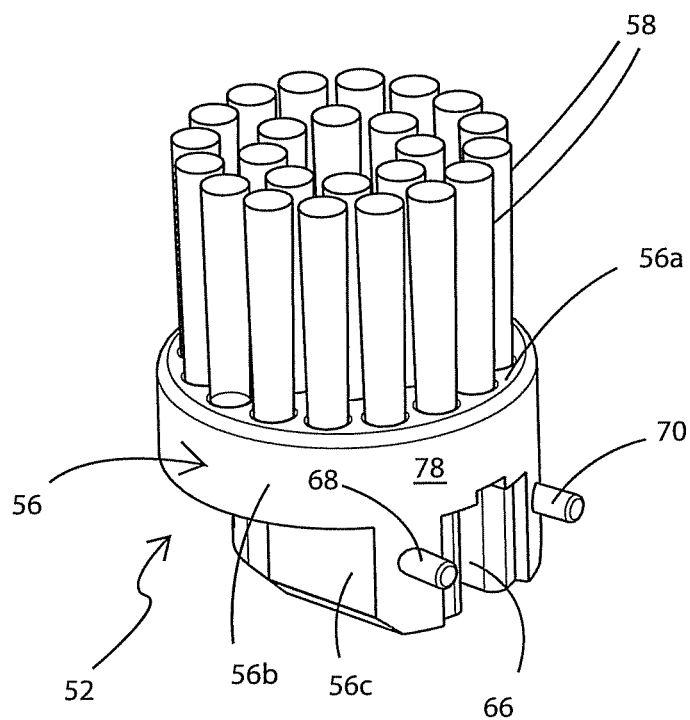
FIG. 5a is a perspective view of a first bristle block used in the brush head and showing the two drive pins that extend outwardly therefrom.
Figure 5B:
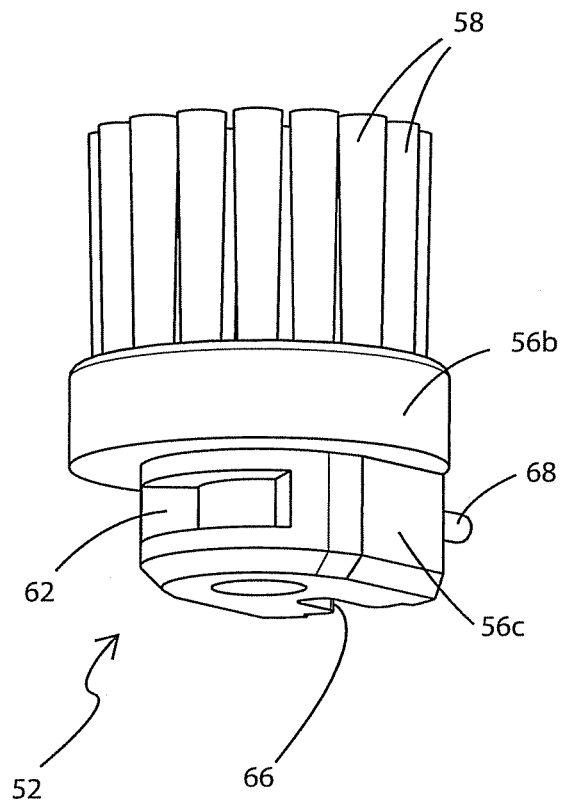

In accordance with a specific feature of the present invention, head 14 is provided with a first bristle block 52 and a second bristle block 54. First and second bristle blocks 52, 54 preferably are disposed adjacent each other but may, alternatively, be spaced a distance apart. First bristle block 52 is configured to engage pivot rod 46 and second bristle block 54 is configured to engage connector member 48. As is best seen in FIGS. 5a and 5b, first bristle block 52 includes a base 56 in which a plurality of first bristles 58 are anchored. First bristles 58 may be individual bristles or tufts of bristles. First bristles 58 extend outwardly from an outer surface 56a of base 56 and generally at right angles thereto. Base 56 includes a first region 56b and a second region 56c. First region 56b is generally circular in shape and is complementary to a first portion 15 of the wall of head 14 that defines opening 44. FIG. 3 shows that when first bristle block 52 is received in opening 44, a top portion of first region 56b is substantially flush with top end 14a of head 14. Additionally, the side areas of first bristle block 52 are generally flush with the side areas of head 14 (FIG. 1). FIG. 3 also illustrates that first portion 15 of the wall of head 14 which defines opening 44 is recessed relative to a second portion 17 thereof. First bristle block 52 is configured to fit within this recessed first portion 15 and second bristle block 54 is configured to fit within the second portion 17.

Figure 8:
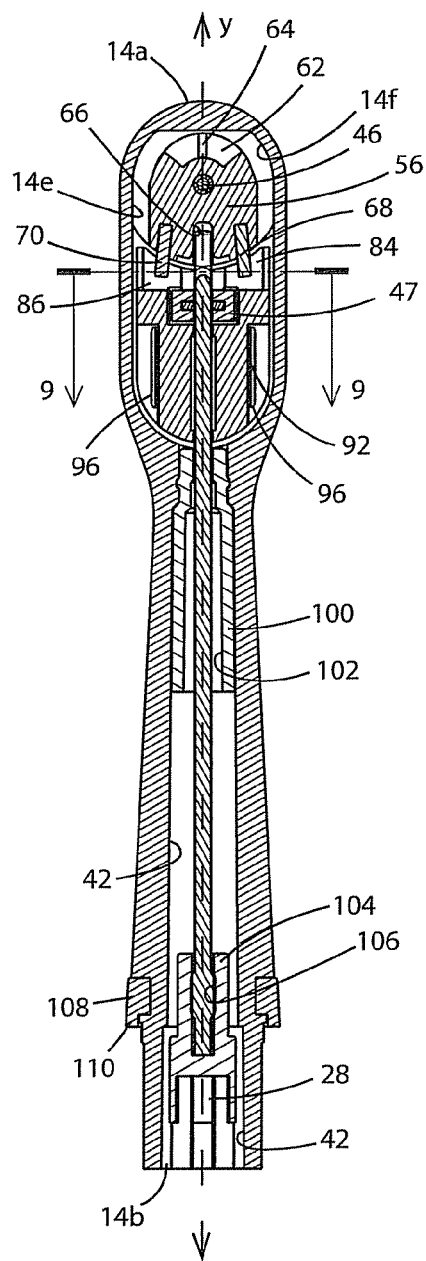
FIG. 8 is a cross-sectional rear view of the brush head taken through line 8-8 of FIG. 3.

Second region 56c of first bristle block 52 is configured to be received through opening 44 and into cavity 42 of head 14. FIG. 7 shows that base 56 further defines a first slot 60 therein within which pivot rod 46 is received. Second region 56c of base 56 defines a second slot 62 within which a connector pin 64 is received. Second slot 62 extends radially inwardly from the outermost surface of second region 56c and toward pivot pin 46. Connector pin 64 extends through an aperture (not numbered) in top end 14a of head 14 and into second slot 62. FIGS. 5b and 8 show that second slot 62 is arcuate in shape and extends along substantially most of the top end of second region 56c. Pivot rod 46 and connector pin 64 retain first bristle block 52 in head 14.

It should be noted that second region 56c of base 56 is smaller in dimension that first region 56b thereof. This, in combination with the configuration of second region 56c, permits first bristle block 52 to rotate to a limited degree around pivot rod 46. Since pivot rod 46 is disposed at right angles to longitudinal axis "Y" of head 14, the rotation of first bristle block 52 is at right angles to longitudinal axis "Y".

Figure 10:
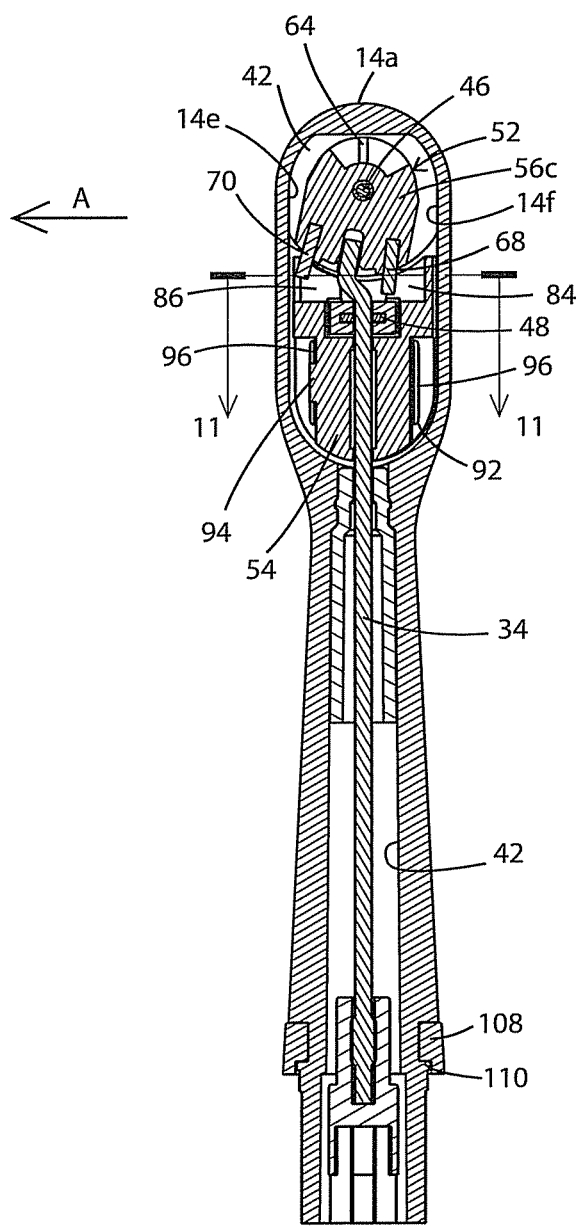
FIG. 10 is a cross-sectional rear view of the brush head taken through line 8-8 of FIG. 3 and showing the first bristle block in a first position.
Figure 12:
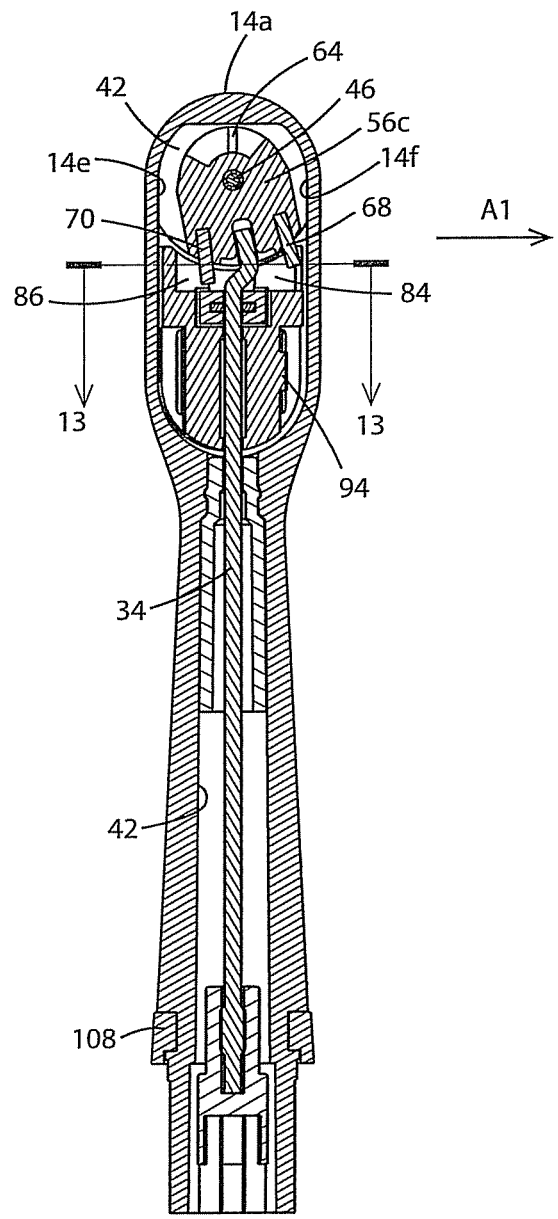
FIG. 12 is a cross-sectional rear view of the brush head taken through line 8-8 of FIG. 3 and showing the first bristle block in a second position.

FIGS. 8, 10 and 12 show that the rotation of first bristle block 52 is limited in nature, with the rotation being limited by engagement of the sides of second region 56c with the interior walls 14e, 14f of head 14.

In accordance with another feature of the present invention, base 56 defines a third slot 66 within which a second end 34b (FIG. 4) of driveshaft 34 is received. Driveshaft 34 has a longitudinal axis that is substantially identical to longitudinal axis "Y" of head 14. Second end 34b is offset with respect to the longitudinal axis "Y" and therefore acts as a cam. Third slot 66 is a closed-end slot that extends radially inwardly from the outermost wall of second region 56c of base 56 and terminates a distance from pivot rod 46. Third slot 66 is of a sufficient width and length to allow second end 34b of driveshaft 34 to rotate therein through 360°. The rotating second end 34b engages the interior surfaces of those portions of second region 56c that define third slot 66 and thereby causes first bristle block 52 to move. As indicated previously, first bristle block 52 rotates or pivots about the axis formed by pivot rod 46. More particularly, rotation of driveshaft 34 causes first bristle block 52 to be moved along a circular path about pivot rod 46.

In accordance with yet another feature of the present invention, base 56 further includes a first projection 68 and a second projection 70 that extend outwardly and downwardly from second region 56c thereof. Preferably, first and second projections 68, 70 are metal pins. FIG. 5a shows that first and second projections 68, 70 are spaced a distance from each other and they flank third slot 66. As is best shown in FIG. 8, each of first and second projections 68, 70 preferably is disposed at an acute angle relative to the longitudinal axis "Y" of head 14. Preferably, the angle is around 5° relative to longitudinal axis "Y". When first bristle block 52 is engaged on pivot rod 46, first and second projections 68, 70 extend downwardly toward bottom end 14b of head 14 and into contact with second bristle block 54.

Figure 6A:
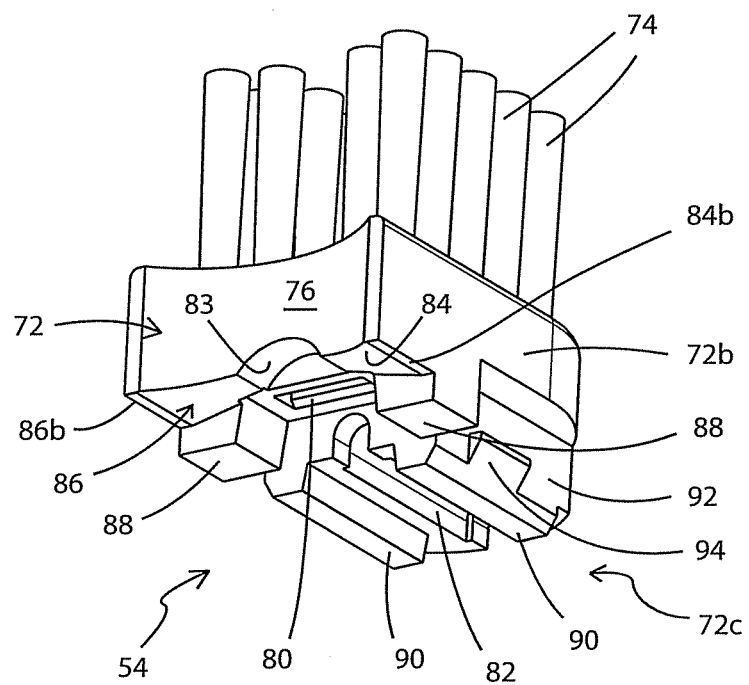
FIG. 6a is a perspective view of a second bristle block used in the brush head.
Figure 6B:
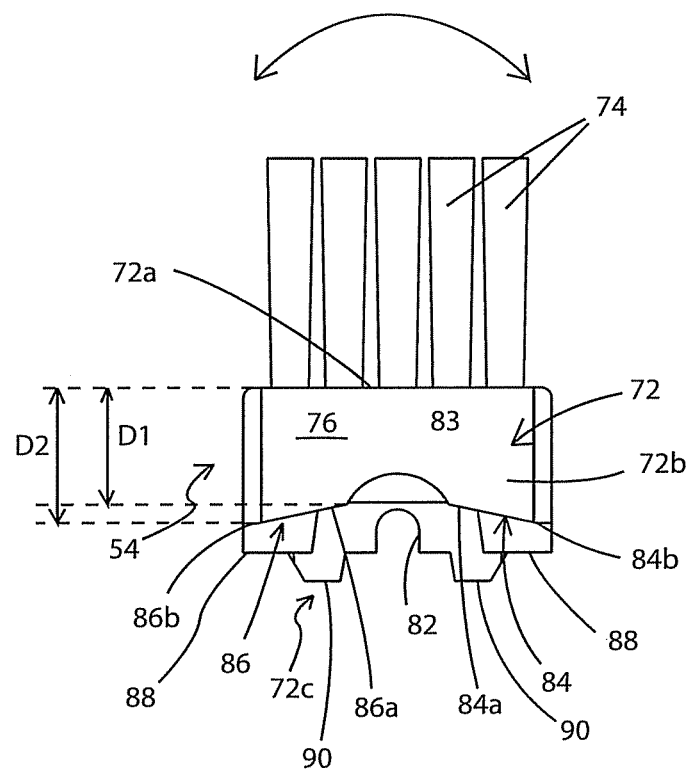

Referring to FIGS. 6a and 6b, and in accordance with another specific feature of the present invention, second bristle block 54 includes a base 72 in which a plurality of second bristles 74 are anchored. Second bristles 74 extend outwardly from an outer surface 72a of base 72 and are disposed substantially at right angles thereto. Second bristles 74 may be individual bristles or may be tufts of bristles. Base 72 includes a first region 72b that is complementary to second portion 17 of the wall that defines opening 44. First region 72b of base 72 includes an arcuate portion 76 (FIG. 4) that is complementary to a lowermost portion 78 of base 56 of first bristle block 52. Thus, when first and second blocks 52, 54 are received in opening 44, arcuate portion 76 is disposed in abutting contact with lowermost portion 78. Additionally, when second bristle block 54 is engaged in head 14, first region 72b of base 72 is substantially flush with the exterior surfaces of first region 56b of base 56 on first bristle block 52 and with the sides of head 14.

Base 72 of second bristle block 54 includes a second region 72c (FIG. 6a) that is smaller in dimensions than is first region 72b thereof. This enables second region 72c to be received through opening 44 and into cavity 42 in head 14. Base 72 further defines a slot 80 therein that is complementary configured to receive connector member 48 therethrough. Base 72 defines a semi-circular channel 82 therein that extends from a lowermost end of second region 72c and terminates adjacent slot 80. Channel 82 is complementary configured to receive a length of driveshaft 34 therein. Connector member 48 preferably is also configured to permit a portion of driveshaft 34 to pass therethrough. First region 72b of second bristle block 54 defines a semi-circular recess 83 that has a larger radius of curvature than channel 82. Recess 83 is provided to accommodate the rotating second end 34b of driveshaft 34.

In accordance with yet another feature of the present invention, the interior wall of first region 72b includes a first ramp 84 and a second ramp 86 that are disposed on either side of recess 83. First and second ramps 84, 86 are disposed at an obtuse angle relative to each other. An interior end 84a of first ramp 84 is spaced a distance "D1" from outer wall 72b. An outer end 84b of first ramp 84 is spaced a distance "D2" from outer wall 72b. Similarly, an interior end 86a of second ramp 86 is spaced a distance "D1" from outer wall 72b and outer end 86b of second ramp 86 is spaced a distance "D2" from outer wall 72b. Thus, first and second ramps 84, 86 flare outwardly away from recess 83 and from each other. When first and second bristle blocks 52, 54 are engaged with head 14, first projection 68 engages first ramp 84 and second projection 70 engages second ramp 86. Consequently, second bristle block 54 is operatively engaged with first bristle block 52. As will be further described herein, movement of first bristle block 52 in response to rotation of driveshaft 34 about longitudinal axis "Y" causes second bristle block 54 to be moved. This movement is caused by first and second projections 68, 70 traveling across ramps 84, 86 as first bristle block 52 is rotated about pivot pin 46. The rotation of driveshaft 34 absent first bristle block 52 cannot cause motion of second bristle block 54 because the driveshaft 34 simply rotates within channel 82. There are no additional cams along driveshaft 34 between first end 34a and second end 34b that could engage second bristle block 54.

Second bristle block 54 further includes stops 88 and ridges 90 that may aid the block in moving within opening 44. Ridges 90 are configured to run substantially parallel to channel 82 and therefore when second bristle block 54 is engaged with head 14, ridges 90 are disposed substantially parallel to longitudinal axis "Y". Second bristle block 54 also defines a recessed area 92 on each of the sides of the block. Each recessed area 92 includes a detent 94 (FIG. 6a) that projects laterally outwardly from the side of second region 72c. A pair of securing members 96 is provided to engage second bristle block 54 and aid in securing the same in opening 44. Each securing member 96 defines an aperture 98 therein that is complementary to one of the detents 94. When each securing member 96 is engaged in one of recessed areas 92, detent 94 protrudes through aperture 98.

Referring to FIGS. 4 and 7, a support member 100 is provided in cavity 42 of head 14. Support member 100 defines an interior bore 102 sized to receive driveshaft 34 therethrough. The exterior configuration of support member 100 is complementary to the interior configuration of cavity 42 proximate second bristle block 54. Support member 100 serves to maintain driveshaft 34 in the correct position and orientation relative to first and second bristle blocks 52, 54 and to ensure that driveshaft 34 does not move back and forth between the interior surfaces of front region 14c and back region 14d of head 14. Head 14 further includes a coupling member 104. Coupling member 104 defines a first bore 106 therein that is designed to secure first end 34a of driveshaft 34 therein. Coupling member 104 also engages a short section of motor driveshaft 28 therein in such a manner that rotational motion of motor driveshaft 28 is transferred to coupling member 104 and thereby to driveshaft 34. Coupling member 104 is also configured to interlockingly engage with connector 30 in handle 12. A finishing ring 108 is received in a groove 109 formed adjacent an annular shoulder 110 on head 14. Ring 108 is provided to both hide and seal the connection between handle 12 and head 14.

As is shown in FIG. 3, bottom end 14b of head 14 is of a reduced diameter relative to that portion of head 14 immediately above groove 109. The diameter of bottom end 14b is complementary to the diameter of opening 36 in top end 12c of handle 12. Bottom end 14b of head 14 is provided with a detent latch 112 that is configured to releasably engage a shoulder 114 in the interior of handle 12. When bottom end 14b of head 14 is received in opening 36 and latch 112 is engaged with shoulder 114, head 14 and handle 12 are engaged with each other and toothbrush 10 can be used to brush a user's teeth.

Figure 9:
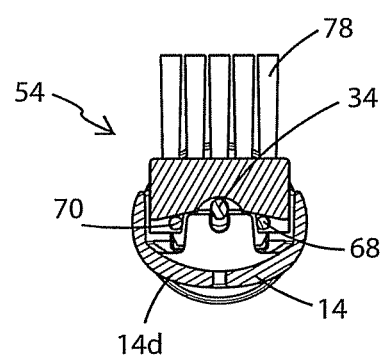
FIG. 9 is a cross-section top view of the brush head taken through line 9-9 of FIG. 8.

Toothbrush 10 is used in the following manner. The user activates brush 10 by engaging on/off switch 18 on handle 12. This engagement causes motor 26 to be activated. Motor 26 causes motor driveshaft 28 to rotate about the longitudinal axis "Y" and this rotational motion is passed to driveshaft 34 through coupling member 104. Consequently, driveshaft 34 also rotates about longitudinal axis "Y" through 360°. Since second end 34b is offset relative to the rest of driveshaft 34b and thereby forms a cam, and since second end 34b is disposed in third slot 66 in first bristle block 52, the rotation of this cam causes motion in said first bristle block 52. This motion is illustrated in FIGS. 8 through 13. FIGS. 8 and 9 show the position of second end 34b of driveshaft 34 and the position of first bristle block 52 when driveshaft 34 is in a neutral position, such as when motor 26 is not activated. In this neutral position, first and second projections 68, 70 are spaced equidistantly from second end 34b. Both of the first and second bristle blocks 52, 54 are centered between interior walls 14e and 14f of head 14, outer wall 72a of base 72 is equidistant from each of interior walls 14e and 14f (FIG. 9), and first and second projections 68, 70 are positioned generally in a central region of ramps 84 and 86, respectively.

Figure 11:
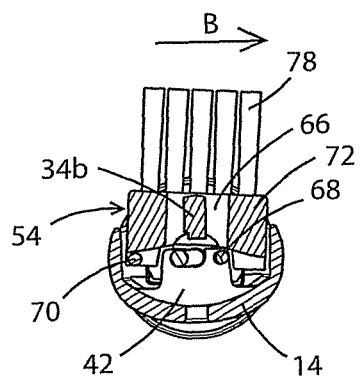
FIG. 11 is a cross-sectional top view of the brush head taken through line 11-11 of FIG. 10.

FIGS. 10 and 11 illustrate the situation where driveshaft 34 has rotated through 90° from the neutral position. Since second end 34b of driveshaft 34 contacts one of the interior walls of base 56 that define third slot 66, first bristle block 52 has been rotated about pivot rod 46 until a portion of first bristle block 52 contacts interior side wall 14e of head 14. In this position, first bristle block 52 has been rotated about pivot rod 46 through about 25° in a first direction. As shown in FIG. 10, this rotational motion of first bristle block 52 is in a clockwise direction and bristles 58 on first bristle block 52 are moved through a clockwise arc of about 25° along the surface of any teeth they may be in contact with. The rotation of first bristle block 52 also causes first and second projections 68, 70 to slide along ramps 84, 86 in a first direction indicated by arrow "A" in FIG. 10. The sliding motion of the projections on the ramps causes second bristle block 54 to be moved from the neutral position (FIG. 9) to a first position where the left side of base 72 of block 54 (with reference to the drawings) extends further outwardly from head 14 than does the right side thereof. Essentially, second bristle block 54 pivots about driveshaft 34 because the driveshaft passes through channel 82 on second bristle block 54. It should be noted, however, that driveshaft 34 does not directly cause any motion of second bristle block 54; it simply rotates within the channel 82 and second bristle block 54 rotates about the longitudinal axis "Y" of driveshaft 34. This movement of second bristle block 54 causes bristles 74 thereon to sweep laterally across any teeth they are in contact with. In the drawing shown in FIG. 11, this is illustrated by bristles being moved toward the right as indicated by arrow "B". It should also be noted that outer surface 72a of second bristle block 72 is moved through an angle "C" of around 10° in a first direction relative to its neutral position.

Shaft 34 continues its rotation about longitudinal axis "Y" and when it has rotated an additional 90°, both of the first bristle block 52 and second bristle block 54 return to the neutral position (FIGS. 8&9). This return to neutral causes first bristle block 52 to pivot back through about 25° thereby moving first bristles 58 in an arc in the opposite direction to their first motion. Additionally, second bristles 74 sweep laterally across any teeth they are in contact with in the opposite direction to arrow "B". (In other words, with reference to FIG. 11, the second bristles 74 move back toward the left until they are in the position shown in FIG. 9 once more.)

Figure 13:
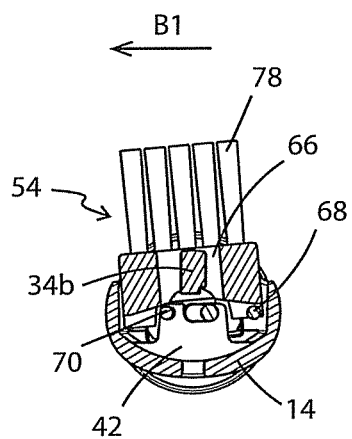
FIG. 13 is a cross-sectional top view of the brush head taken through line 13-13 of FIG. 12.

Shaft 34 continues its rotation about longitudinal axis "Y" and when it has rotated through an additional 90°, both of the first bristle block 52 and second bristle block 54 are in the positions illustrated in FIGS. 12 & 13. First bristle block 52 is in a second position where it has rotated through 25° in a counterclockwise direction relative to the neutral position, thereby moving first bristles 58 through a counterclockwise arc across the teeth. This rotational motion of first bristle block 52 also causes first and second projections 68, 70 to slide along ramps 84, 86 in a second direction indicated by arrow "A1" (FIG. 12). This direction "A1" is opposite to the direction indicated by arrow "A". The sliding of projections 68, 70 along ramps 84, 86 in turn causes second bristle block 54 to move in the opposite direction to that shown in FIG. 11, so that the left hand side of second bristle block 54 extends further into cavity 42 in head 14 than does the right hand side thereof. Furthermore, the motion causes outer surface 72a of base 72 to be disposed at an angle "C1" of about 10° relative to the neutral position and in the opposite orientation to angle "C". The motion of second bristle block 54 causes second bristles 74 to sweep laterally across any teeth they are in contact with in a direction indicated by arrow "B1". This direction "B1" is opposite to the direction "B". It should be noted that the second bristle block 54 rocks back and forth through about 10° in each of the first and second directions as driveshaft 34 rotates. Consequently, second bristle block 54 rocks back-and-forth through a total of about 20° altogether. Additionally, the motion is not parallel to pivot rod 46, it is instead at right angles thereto. This type of motion is advantageous in that it causes second bristles to sweep laterally back and forth across the user's teeth.

The driveshaft 34 continues its rotation through 360° by passing through another 90°. This motion returns first and second bristle blocks 52, 54 to the neutral position shown in FIGS. 8 &9, thereby sweeping first and second bristles 58, 78 in the opposite directions to those produced by the previous rotation. This cycle is repeated as driveshaft 34 continues to rotate through 360° until the user pushes the on/off switch 18 again to deactivate motor 26. The rotation of the driveshaft 34 therefore produces a rotational motion in first bristle block 52 and a rocking back-and-forth motion in second bristle block 54. Consequently, rotation of the driveshaft 34 produces both a circular cleaning motion by first bristles 58 and a sweeping side-to-side motion of second bristles 74. Rotation of driveshaft 34 through 360° and about longitudinal axis "Y" therefore causes a first type of motion in first bristle block 52 and through that movement of first bristle block 52 causes a second type of motion in second bristle block 54.

Brush head 14 in accordance with the present invention therefore includes a body having a first bristle block 52 engaged therein and having a plurality of bristles 58 extending outwardly from a first face 56a thereof, a second bristle block 54 disposed adjacent first bristle block 52 in the body and having a plurality of bristles 74 extending outwardly from a first face 72a thereof, a rotatable driveshaft 34 having a longitudinal axis "Y" and a cam 34b, wherein cam 34b engages first bristle block 52 to move the same about an axis (pivot rod 46) disposed generally perpendicular to the longitudinal axis "Y" of driveshaft 34; and wherein first bristle block 52 engages second bristle block 54 and causes the same to oscillate about the longitudinal axis "Y" of driveshaft 34, wherein second bristle block 54 moves in a direction generally perpendicular to the axis (pivot rod 46) of first bristle block 52.

It will be understood that while the above disclosure has indicated that the first bristle block 52 is caused to rotate by the driveshaft 34 and the second bristle block 54 is caused to rock back-and-forth or oscillate by the first bristle block 52, other motions of these two bristle blocks are contemplated to fall within the scope of the present invention. For example, the first bristle block may be caused to rotate and the second bristle block may be caused to move linearly back and forth along driveshaft 34, Alternatively, the first bristle block may be caused to move linearly and the second bristle block may be caused to rotate. It is even contemplated that the same type of motion may be caused in each of the first and second blocks but that motion occurs in different orientations. It is desirable, however, that the driveshaft 34 drives only one of the first and second bristle blocks to effect these motions.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A brush head comprising:
   a body adapted to be connected to a powered handle;
   a bore extending through the body;
   a driveshaft extending through the bore and rotatable about a longitudinal axis, said driveshaft having a first end and a second end, the first end being adapted to be operatively connected to a motor disposed in the handle;
   a first bristle block disposed in the body and being operatively engaged with the driveshaft; wherein the first bristle block includes:
      a circumferential wall;
      a radial slot defined in the circumferential wall and extending inwardly toward a central axis; wherein the second end of the driveshaft is received in the radial slot; and
      a first projection and a second projection extending outwardly away from the circumferential wall and spaced a distance from each other;
   a second bristle block disposed in the body and being operatively engaged with the first bristle block; wherein rotation of the driveshaft produces a first type of motion in the first bristle block, and the motion of the first bristle block produces a second type of motion in the second bristle block; wherein said second bristle block includes a first end wall inclined at an angle relative to the longitudinal axis of the head and having a first ramp and a second ramp spaced from the first ramp, wherein the first projection on the first bristle block engages the first end wall of the second bristle block and the first projection travels along the first ramp when the first bristle block moves and the movement of the first projection along the first ramp is reciprocal; and the second projection engages the second ramp and moves reciprocally therealong when the first bristle block is moved.

2. The brush head as defined in claim 1, wherein the rotation of the driveshaft causes a rotational motion in the first bristle block and a back-and-forth rocking motion in the second bristle block.

3. The brush head as defined in claim 2, wherein the second bristle block moves reciprocally between a first direction and a second direction, and wherein the second bristle block moves through about 10° in the first direction relative to a neutral position, and through about 10° in the second direction relative to the neutral position.

4. The brush head as defined in claim 2, wherein the rotation of the driveshaft causes the first bristle block to reciprocate back and forth along an arcuate path.

5. The brush head as defined in claim 4, wherein the first bristle block has a neutral position when the driveshaft is at rest, and has a second position and a third position on opposite sides of the neutral position, and the first bristle block reciprocates back and forth between the second and third positions when the driveshaft rotates.

6. The brush head as defined in claim 5, wherein the second position is disposed at an angle of about 25° on a first side of the neutral position and the third position is disposed at an angle of about 25° on a second side of the neutral position.

7. The brush head as defined in claim 1, wherein the motion of the first bristle block is disposed substantially at right angles to the motion of the second bristle block.

8. The brush head as defined in claim 1, wherein the first bristle block is rotatable through an arc of less than 360°.

9. The brush head as defined in claim 8, wherein the first bristle block is rotatable through an arc of about 50°.

10. The brush head as defined in claim 9, wherein the first bristle block is reciprocally rotatable through an arc of about 25° in a clockwise direction and through an arc of about 25° in a counter-clockwise direction for each rotation of the driveshaft through 360°.

11. The brush head as defined in claim 1, wherein rotation of the first bristle block is about an axis disposed substantially at right angles to the longitudinal axis.

12. The brush head as defined in claim 1, wherein the second end of the driveshaft is offset relative to the longitudinal axis and comprises a cam, and wherein the cam is disposed in the radial slot.

13. The brush head as defined in claim 1, wherein the second ramp is inclined in the opposite direction relative to the first ramp.

14. The brush head as defined in claim 13, wherein the first and second ramps are disposed at an obtuse angle relative to each other.

15. The brush head as defined in claim 1, wherein both of the first and second projections comprise metal pins.

16. A powered toothbrush comprising:
a handle having a top end, a bottom end and a wall extending therebetween;
a motor disposed in the handle;
a power source operationally engaged with the motor;
a first driveshaft extending outwardly from the motor and being rotatable by the motor about a longitudinal axis of the handle;
a brush head including:
a body removably connected to the top end of the handle;
a bore extending through the body;
a second driveshaft extending through the bore;
a connector assembly operationally engaging the first driveshaft and the second driveshaft together;
a first bristle block disposed in the body and being operatively engaged with the second driveshaft; wherein the first bristle block includes;
a circumferential wall;
a radial slot defined in the circumferential wall and extending inwardly toward a central axis; wherein the second end of the driveshaft is received in the radial slot; and
a first projection and a second projection extending outwardly away from the circumferential wall and spaced a distance from each other;
a second bristle block disposed in the body and being operatively engaged with the first bristle block, wherein rotation of the second driveshaft in response to rotation of the first driveshaft produces a first type of motion in the first bristle block, and the motion of the first bristle block produces a second type of motion in the second bristle block; wherein said second bristle block includes a first end wall inclined at an angle relative to the longitudinal axis of the head and having a first ramp and a second ramp spaced from the first ramp, wherein the first projection on the first bristle block engages the first end wall of the second bristle block and the first projection travels along the first ramp when the first bristle block moves and the movement of the first projection along the first ramp is reciprocal; and the second projection engages the second ramp and moves reciprocally therealong when the first bristle block is moved.

17. The toothbrush as defined in claim 16, wherein the rotation of the second driveshaft causes a rotational motion in the first bristle block and a back-and-forth rocking motion in the second bristle block.

\* \* \* \* \*